(12) United States Patent
Gibby et al.

(10) Patent No.: US 11,266,480 B2
(45) Date of Patent: *Mar. 8, 2022

(54) AUGMENTED REALITY VIEWING AND TAGGING FOR MEDICAL PROCEDURES

(71) Applicant: Novarad Corporation, American Fork, UT (US)

(72) Inventors: Wendell Arlen Gibby, Mapleton, UT (US); Steven Todd Cvetko, Draper, UT (US)

(73) Assignee: Novarad Corporation, American Fork, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/201,983

(22) Filed: Mar. 15, 2021

(65) Prior Publication Data
US 2021/0298866 A1    Sep. 30, 2021

Related U.S. Application Data

(63) Continuation of application No. 16/486,818, filed as application No. PCT/US2018/019024 on Feb. 21, (Continued)

(51) Int. Cl.
    *A61B 90/00*    (2016.01)
    *G16H 30/20*    (2018.01)
    (Continued)

(52) U.S. Cl.
    CPC .......... *A61B 90/36* (2016.02); *A61B 1/00009* (2013.01); *A61B 1/04* (2013.01);
    (Continued)

(58) Field of Classification Search
    CPC .......... G06T 7/74; G06T 11/00; G06T 19/006; G06T 19/00; G06T 2207/10016;
    (Continued)

(56) References Cited

U.S. PATENT DOCUMENTS 9,119,655 B2 *  9/2015  Bowling ............... A61B 34/74
9,128,909 B2 *  9/2015  Brindley ............ G06Q 30/0256
(Continued)

FOREIGN PATENT DOCUMENTS

| WO | WO 2008/076079 | 6/2008 |
| WO | WO 2014200016 | 12/2014 |
| WO | WO 2016/162789 | 10/2016 |

OTHER PUBLICATIONS

Sutherland et al. "Applying Modem Virtual and Augmented Reality Technologies to Medical Images and Models", Journal of Digital Imaging, Feb. 15, 2019, pp. 38-53. Retrieved on Jun. 17, 2021. Retrieved from URL: https://pubmed.ncbi.nlm.nih.gov/30215180/.
(Continued)

*Primary Examiner* — Abderrahim Merouan
(74) *Attorney, Agent, or Firm* — Thorpe North & Western, LLP.

(57) ABSTRACT

Technology is described for augmenting medical imaging for use in a medical procedure. The method can include the operation of receiving an image of patient anatomy captured by a visual image camera during the medical procedure. An acquired medical image associated with the patient anatomy can then be retrieved. Another operation can be associating the acquired medical image to the patient anatomy. An augmentation tag associated with a location in one layer of the acquired medical image can be retrieved. A further operation can be projecting the acquired medical image and the augmentation tag using an augmented reality headset to form a single graphical view as an overlay to the patient anatomy in either 2D, 3D or holographic form.

19 Claims, 20 Drawing Sheets

Related U.S. Application Data 2018, now Pat. No. 10,945,807, which is a continuation of application No. 15/438,715, filed on Feb. 21, 2017, now Pat. No. 10,010,379.

(51) Int. Cl.

| | |
|---|---|
| *A61B 5/06* | (2006.01) |
| *A61B 5/107* | (2006.01) |
| *A61B 90/96* | (2016.01) |
| *A61B 90/98* | (2016.01) |
| *G02B 27/01* | (2006.01) |
| *G06T 7/73* | (2017.01) |
| *G06T 19/00* | (2011.01) |
| *G06F 3/01* | (2006.01) |
| *A61B 1/04* | (2006.01) |
| *A61B 1/00* | (2006.01) |
| *A61B 90/90* | (2016.01) |
| *A61B 90/94* | (2016.01) |
| *G06T 11/00* | (2006.01) |
| *G16H 30/40* | (2018.01) |
| *G16H 50/50* | (2018.01) |
| *A61B 90/50* | (2016.01) |
| *A61B 34/10* | (2016.01) |
| *A61B 17/00* | (2006.01) |

(52) U.S. Cl.
CPC ........... *A61B 5/066* (2013.01); *A61B 5/1072* (2013.01); *A61B 5/1075* (2013.01); *A61B 90/361* (2016.02); *A61B 90/90* (2016.02); *A61B 90/94* (2016.02); *A61B 90/96* (2016.02); *A61B 90/98* (2016.02); *G02B 27/017* (2013.01); *G06F 3/011* (2013.01); *G06F 3/012* (2013.01); *G06F 3/017* (2013.01); *G06T 7/74* (2017.01); *G06T 11/00* (2013.01); *G06T 19/006* (2013.01); *G16H 30/20* (2018.01); *G16H 30/40* (2018.01); *G16H 50/50* (2018.01); *A61B 2017/00207* (2013.01); *A61B 2017/00216* (2013.01); *A61B 2034/101* (2016.02); *A61B 2090/363* (2016.02); *A61B 2090/365* (2016.02); *A61B 2090/372* (2016.02); *A61B 2090/373* (2016.02); *A61B 2090/374* (2016.02); *A61B 2090/376* (2016.02); *A61B 2090/378* (2016.02); *A61B 2090/3762* (2016.02); *A61B 2090/502* (2016.02); *G06T 19/00* (2013.01); *G06T 2207/10016* (2013.01); *G06T 2207/10068* (2013.01); *G06T 2207/30204* (2013.01); *G06T 2210/41* (2013.01)

(58) Field of Classification Search
CPC . G06T 2207/10068; G06T 2207/30204; G06T 2210/41; G16H 50/50; G16H 30/20; G16H 30/40; G02B 27/017; G06F 3/011; G06F 3/012; G06F 3/017; G06F 19/321; A61B 90/36; A61B 90/361; A61B 90/96; A61B 1/04; A61B 5/066; A61B 5/1072; A61B 5/1075; A61B 2090/372; A61B 2090/373; A61B 2090/374; A61B 2090/3762; A61B 2090/378; A61B 2090/502

See application file for complete search history.

(56) References Cited

U.S. PATENT DOCUMENTS

| | | | |
|---|---|---|---|
| 9,161,824 B2* | 10/2015 | Chishti | A61C 7/00 |
| 10,929,670 B1 | 2/2021 | Troy et al. | |
| 2005/0259882 A1* | 11/2005 | Dewaele | G06T 7/75 |
| | | | 382/243 |
| 2005/0262031 A1* | 11/2005 | Saidi | G16H 50/20 |
| | | | 706/21 |
| 2007/0060799 A1 | 3/2007 | Lyon et al. | |
| 2007/0066881 A1 | 3/2007 | Edwards et al. | |
| 2007/0090197 A1 | 4/2007 | Senda | |
| 2007/0167735 A1 | 7/2007 | Zhong et al. | |
| 2008/0208041 A1* | 8/2008 | Gilboa | A61B 6/12 |
| | | | 600/426 |
| 2008/0269664 A1 | 10/2008 | Trovato et al. | |
| 2009/0078772 A1 | 3/2009 | Ofek et al. | |
| 2010/0049548 A1* | 2/2010 | Kubota | G06Q 10/10 |
| | | | 705/3 |
| 2010/0099980 A1 | 4/2010 | Godara et al. | |
| 2011/0105895 A1* | 5/2011 | Kornblau | A61B 34/20 |
| | | | 600/426 |
| 2011/0268248 A1 | 11/2011 | Simon et al. | |
| 2012/0078236 A1* | 3/2012 | Schoepp | A61B 34/20 |
| | | | 606/1 |
| 2014/0210856 A1 | 7/2014 | Finn et al. | |
| 2014/0275760 A1* | 9/2014 | Lee | A61B 34/30 |
| | | | 600/102 |
| 2014/0355840 A1* | 12/2014 | Pearson Peyton | G06T 7/0014 |
| | | | 382/115 |
| 2015/0161802 A1 | 6/2015 | Christiansen | |
| 2015/0173715 A1* | 6/2015 | Raghavan | A61B 8/565 |
| | | | 600/440 |
| 2016/0035139 A1* | 2/2016 | Fuchs | G06T 7/60 |
| | | | 345/633 |
| 2016/0143699 A1 | 5/2016 | Tanji | |
| 2016/0180441 A1* | 6/2016 | Hasan | G06Q 30/0643 |
| | | | 705/26.7 |
| 2016/0220393 A1* | 8/2016 | Slivka | A61F 2/4675 |
| 2016/0249989 A1 | 9/2016 | Devam et al. | |
| 2016/0270853 A1* | 9/2016 | Lavallee | A61F 2/389 |
| 2017/0045938 A1* | 2/2017 | Aoyama | G16H 50/20 |
| 2017/0116729 A1 | 4/2017 | Stolka et al. | |
| 2017/0178540 A1* | 6/2017 | Rios | G09B 23/285 |
| 2017/0296292 A1 | 10/2017 | Mahmood et al. | |
| 2017/0368369 A1 | 12/2017 | Heinrich et al. | |
| 2018/0064385 A1 | 3/2018 | Schwartz | |
| 2018/0177403 A1 | 6/2018 | Kim-Whitty | |
| 2018/0247128 A1 | 8/2018 | Alvi et al. | |
| 2019/0015009 A1 | 1/2019 | Dyer et al. | |
| 2020/0145495 A1 | 5/2020 | Coffey et al. | |
| 2020/0186786 A1 | 6/2020 | Gibby et al. | |
| 2020/0188030 A1 | 6/2020 | Kopper et al. | |

OTHER PUBLICATIONS

"QR code tracking," Microsoft Hololens Documentation, obtained at https://docs.microsoft.com/en-us/windows/mixed-reality/qr-code-tracking, Oct. 18, 2021.

Microsoft Hololens for Developers, Full Document, Microsoft Hololens Documentation, obtained at https://docs.microsoft.com/en-us/windows/mixed-reality/qr-code-tracking, Oct. 18, 2021.

* cited by examiner

AUGMENTED REALITY VIEWING AND TAGGING FOR MEDICAL PROCEDURES

PRIORITY DATA

This application is a continuation of Ser. No. 16/486,818, filed Aug. 16, 2019, which is a 371 Nationalization of International Application No. PCT/US2018/019024, filed Feb. 21, 2018, which claims benefit of U.S. patent application Ser. No. 15/438,715, filed Feb. 21, 2017, all of which are incorporated herein by reference.

BACKGROUND

Mixed or augmented reality is an emerging area of computing technology where images from the physical world and virtual computing worlds may be combined into a mixed reality world. Mixed reality may encompass a wide range of technological combinations that previously were considered to be only physical reality or only virtual reality. In mixed reality, people, places, and objects from physical and virtual worlds merge together in a blended environment. A mixed reality experience may be enabled through existing commercial operating systems or custom operating systems along with the use of a compatible VR (virtual reality) or AR (augmented reality) headset.

Augmented reality (AR) is an example of mixed reality where a live direct view or an indirect view of a physical, real-world environment is augmented or supplemented by computer-generated sensory input such as sound, video, graphics or even global positioning data. As a result, the technology can enhance a viewer's current perception of reality. Augmentation is conventionally performed as a real world location is being viewed and in semantic context with environmental elements. With the help of advanced AR technology (e.g. adding computer vision and object recognition) the information about the surrounding real world of the user becomes interactive and may be digitally manipulated. Information about the environment and its objects may be overlaid on the real world. This information overlaid on the real world can be virtual images or real information. Augmented reality can bring the components of the digital world into a person's perceived real world.

DETAILED DESCRIPTION

This technology can provide a system and method for using mixed reality or augmented reality devices to improve surgical, interventional radiologic, cardiac, or other medical procedures. An augmented reality device, such as an augmented reality (AR) headset, may be used to overlay acquired medical images or virtual images onto a real world scene (e.g., what user is viewing in the real world) using images projected on lenses or a screen that is partially transparent. In the case of surgical procedures, already acquired medical images may be used as overlay images for viewable patient anatomy. These acquired medical images may be MRI (magnetic resonance imaging), fluoroscopy, CT (computed tomography), sonography, nuclear medicine, computer generated images (CGI), photos, video, or other types of acquired or synthesized medical images. An example of synthesized medical images would be an anatomic atlas overlay on the patient's anatomy to guide surgery. The acquired medical images can be projected onto the lenses of the AR headset in a location that orients the acquired medical images over an appropriate portion of the patient anatomy of the patient being treated.

The overlay of an acquired medical image can assist a surgeon, doctor or other medical professionals in more accurately performing a treatment or operation upon a patient's anatomy. One issue that faces doctors and other medical professionals when performing operations upon patients is making sure the correct patient anatomy is being operated upon. If the wrong person, wrong appendage or wrong location is being operated, on then a poor outcome may be the result. The present technology provides augmented reality tags to more accurately identify patient anatomical structures. Patient identifiers (e.g., physical identifiers) that are affixed to the patient may also be captured and the patient identifiers may be used to load related acquired medical images and augmented reality tags for a patient procedure. Examples would be bar codes, QR codes, patient IDs, physical tags, etc. Morphometric data can also be captured from viewing of a patient's anatomy in the real world and then the morphometric data can be compared with stored morphometric data for an appendage or anatomical structure to be treated. When the morphometric data matches, then the treatment may proceed. Otherwise an error may be flagged based on the morphometric data. Either of these methods (e.g., patient identifiers or morphometric data) can be used to uniquely identify the patient and the area of anatomy to be treated.

Figure 1A:
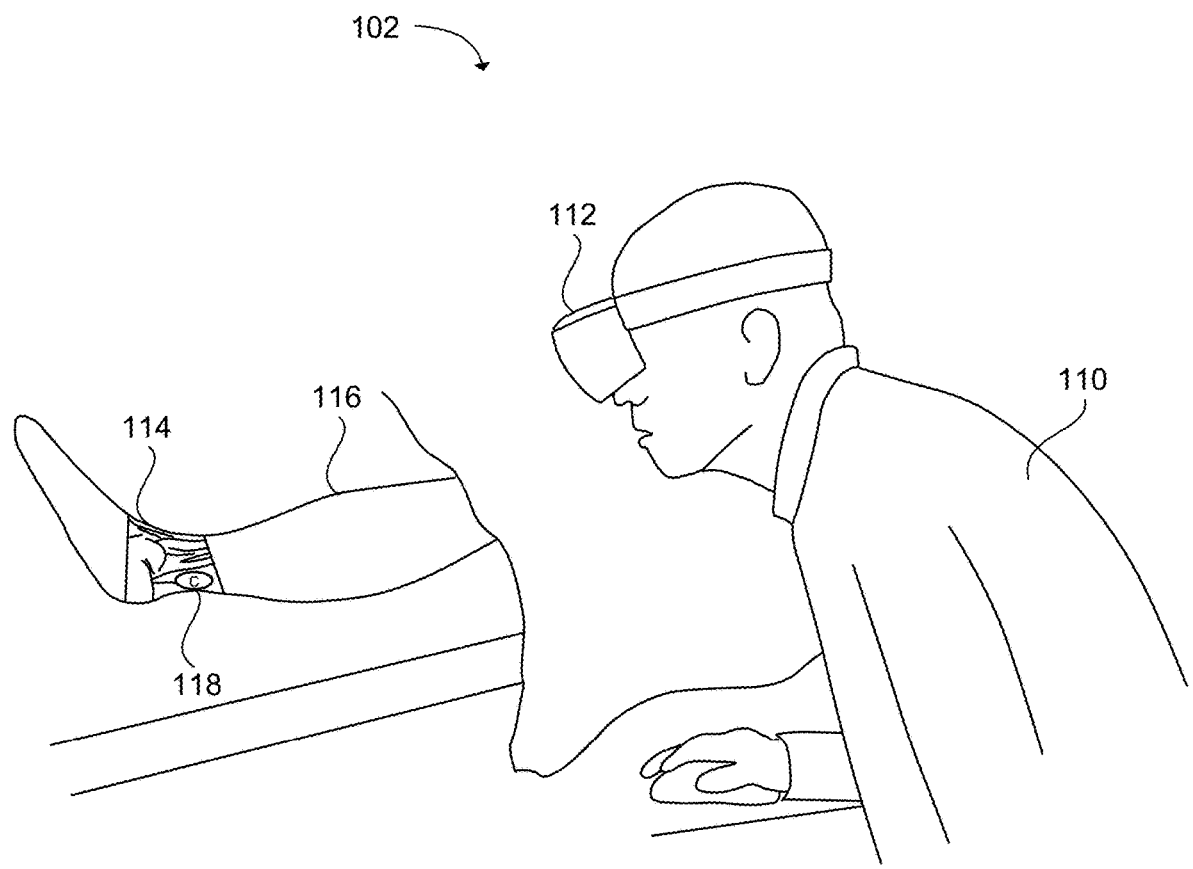
FIG. 1A is an illustration of an example use of an augmented reality head set to augment a medical procedure with acquired medical images.

FIG. 1A illustrates a doctor or medical professional 110 who may be using an AR headset 112. In one example the AR headset 112 may enable a medical professional to see through lenses where an augmented reality image or acquired medical image is projected on the semi-transparent lenses. As a more specific example, an MRI image may be overlaid in an area where an operation is going to occur. The overlaid image results in a compositing of views with a real world scene that is being viewed through the semi-transparent lenses or a semi-transparent optical imaging area. A facet of this ability to overlay images is the cameras that exist in the augmented reality headset to create a contextual map of the space in which the patient lies and allows 3D patient data such as a hologram of images obtained prior to surgery to be merged with the real world of patient anatomy.

In order to augment a medical procedure or surgery with an augmented medical image, a medical doctor or other medical professionals may set up an AR headset 112 in a surgery area 102. A processor associated with the AR headset 112 may receive an image of patient anatomy 116 using a visual image camera in the AR headset 112. An acquired medical image 114 associated with the patient anatomy can then be retrieved. This acquired medical image may be an MRI or CT image that is fed via a wireless connection to the processors and memory in the AR headset.

The acquired medical image 114 can then be associated with or anchored to the patient anatomy 116 that has been identified by the AR headset 112 in the real world scene or space. The anchoring may include fixing or anchoring the acquired medical image or other related virtual images (including augmentation controls) to a fixed point in the viewable real world that has been registered by the AR headset 112. Later when a doctor moves view point positions, the acquired medical image 114 can remain fixed in the correct spot with respect to the patient's anatomy and does not move around in the doctor's vision.

An augmentation tag 118 associated with a location in one layer of the acquired medical image 114 or radiological image can also be retrieved. The augmentation tag may be configured to conform to a three dimensional (3D) structure in the acquired medical image 114 or radiological image to identify an anatomical structure associated with a medical procedure to be performed. The augmentation tag may be a simple geometric shape such as a circle, square, triangle or another more complex shape in two dimensions or three dimensions, such as an outline of the anatomy in question.

Figure 1B:
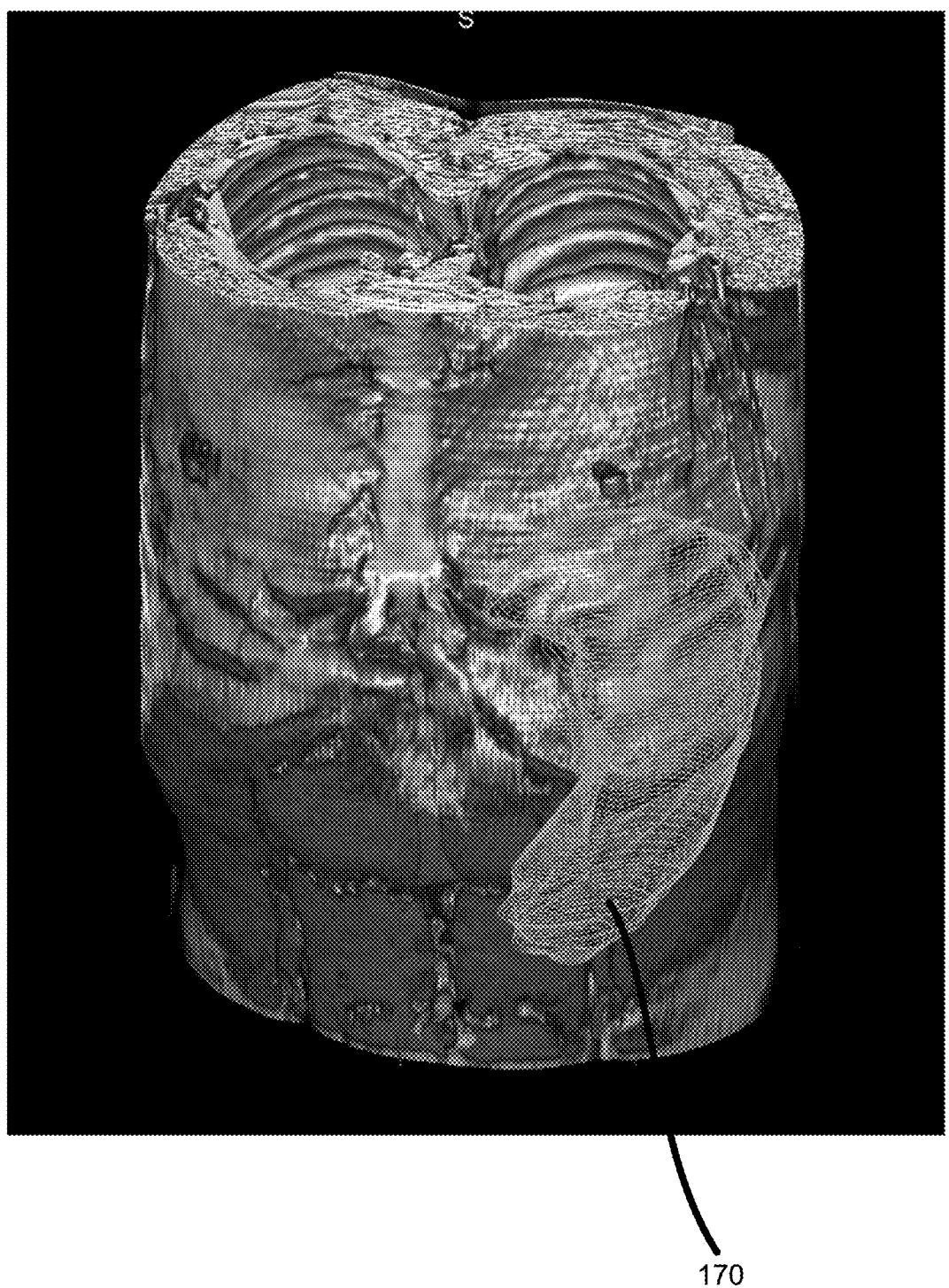
FIG. 1B is an illustration of an example use of a three dimensional augmentation tag for a spleen.

FIG. 1B illustrates that the augmentation tags may be used to pre-label the acquired medical image. If a doctor is going to operate on a patient's spleen 170, then the doctor can apply an augmentation tag to the patient's spleen during diagnosis of a medical condition (e.g., splenomegly or another spleen condition). The augmentation tag may cover a portion of the patient's anatomical structure as loosely marked by the doctor. Then the augmentation processor can then detect the edges of the anatomical structure or use machine pattern recognition and expand or contract the augmentation tag to conform the augmentation tag to the anatomical structure. Later, when the medical procedure, diagnosis or operation is taking place, the doctor can view the tag in the shape of the anatomical structure (e.g., spleen) and be more certain about the positive identification of the structure for treatment.

Figure 1C:
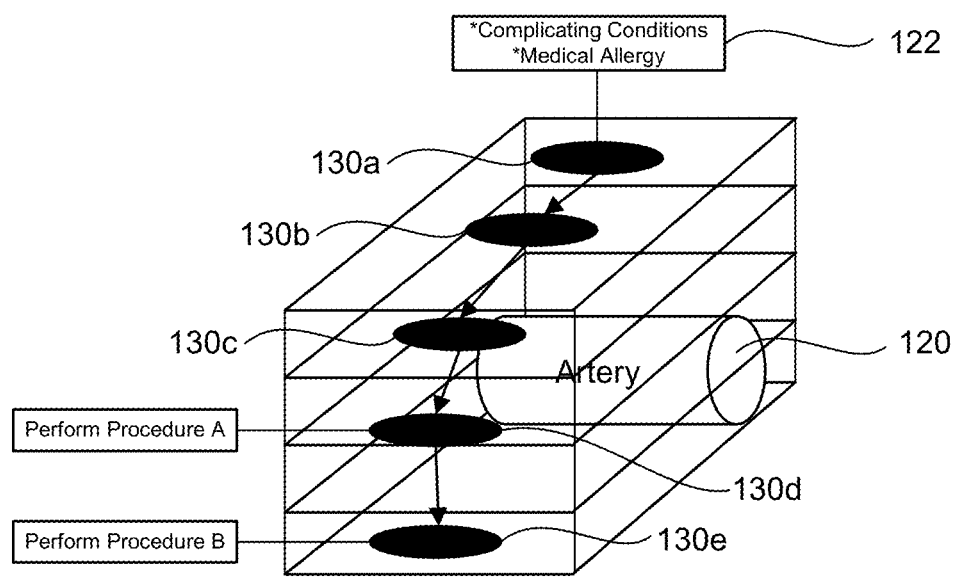
FIG. 1C is an illustration of an example use of a plurality of augmentation tags.

FIG. 1C illustrates that the augmentation tags can be provided in a plurality of anatomical layers of the acquired medical image. For example, the augmentation tags can identify different structures in each layer of the acquired medical images and varying procedures that should occur at those separate layers in the patient's anatomy. In addition, the augmentation tags can be associated to form a tag group 130a-e to guide a surgeon. As a more specific example, there may be a group of diseased anatomical structures that needs to be operated on and these structures can be linked together in an ordered group and the surgeon can be guided from one augmentation tag to the next. This avoids missing any of the anatomy that needs to be operated on or skipping any of the important procedure. Similarly, an ordering may be provided for a surgeon to address different structures in a selected order in order to assist with remembering of any unusual orderings.

In another example, the augmentation tags may guide a surgeon through a safe path to avoid structures, such as an artery 120, which may be delicate or cause problems if the structures are damaged. This way the surgeon can have a mapped path for an operation before the operation begins. A plurality of augmentation tags that are linked together may be used to show a surgical path through the patient's anatomy. For example, the tags may be used to show a surgeon where the surgeon has planned to cut as the surgeon passes through multiple layers. The augmentation tags may also show a surgeon where the surgeon has planned to cut in a lateral direction or travel with an endoscope. This allows to the surgeon to plan out a surgery route in advance and follow that route more accurately during the surgery when using the augmentation tags and the acquired medical image (s). This may reduce the risk of the surgery and improve the overall patient outcome.

In some cases, a plurality of augmentation tags may be linked together to represent one anatomical structure which crosses separate layers of the acquired medical image or radiological image. Thus, each tag may identify that anatomical structure in a separate layer.

Returning to FIG. 1A, the acquired medical image 114 and the augmentation tag(s) 118 can then be projected onto the lenses of the augmented reality headset 112 to form a single graphical view for the medical professional(s) wearing the AR headset 112. As a result, the acquired medical image 114 and augmentation tag 118 may appear as though the images are overlaid directly on the patient anatomy.

In an alternative configuration, the augmentation tag may have a tag extender 122 (FIG. 1B) that can be a geometric shape that extends away from the augmentation tag. Examples of the geometric shape may be a flag, polygon, rectangular box, pyramid or other extension that may display information to a surgeon. The information that may be displayed in the tag extender may identify the procedure to be performed on the anatomy, identify the patient, identify pre-existing patient risks, identify drug allergies, identify known complications or other data that is not directly related to the patient's anatomy but is related to the patient or medical procedure.

Figure 1D:
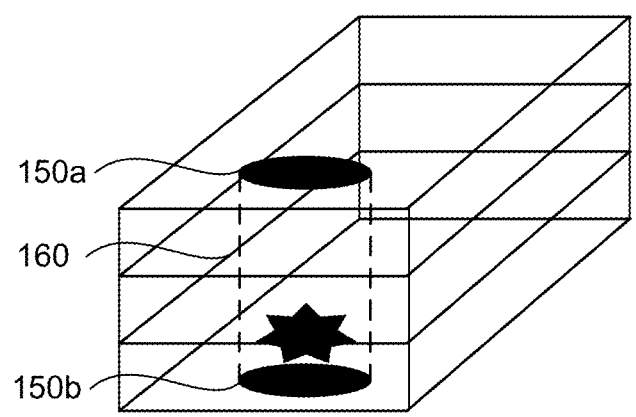
FIG. 1D is an illustration of two dimensional augmentation tags that are automatically made into three dimensional augmentation tags.

Referring now to FIG. 1D, in one further configuration of the augmentation tags, a doctor may create one or more 2D (two dimensional) augmentation tags 150a-b each located on one of a plurality of layers of the acquired medical image. The plurality of 2D (two dimensional) augmentation tags can be automatically joined together by an application to form a 3D augmentation tag or 3D shape that extends through multiple layers of the acquired medical image. For example, a method can be configured to create a 3D shape 160 from the 2D tags. Similarly, the 2D image or one slice of the acquired medical image can be annotated with one or more 2D images, and then the 2D annotations can be expanded to a 3D shape using known 3D shapes such as lines, rectangles, squares, spheres, regular polygons, irregular polygons, or other shapes selectable from a menu. Marking a 3D acquired medical image can be challenging because of the many layers in such images but enabling 2D marking that can be automatically turned into 3D images makes marking of acquired medical images easier for medical professionals. Also, a partial outline of a structure in a patient's anatomy of interest may be drawn and then an application may identify the rest of the anatomical structure using edge and feature detection. This automatic object detection enables a full outline or full shape, as detected by an application, to be used to identify the patient's anatomy to be treated. For example, an organ to be resected can be highlighted with either manual technique, anatomic edge detection or neural networks where the system is trained to find the organ.

The acquired medical image may be a radiological image that is acquired using medical imaging techniques such as a MRI (magnetic resonance imaging), magnetic resonance angiography (MRA), fMRI (function magnetic resonance imaging), mammography, CT (computed tomography), fluoroscopy, X-rays, nuclear medicine (e.g., bone scans, thyroid scans, etc.), PET (positron emission tomography), ultrasound images or any other medical imaging techniques. The acquired medical image may also be an image created using photographic images internal to a human body such as a colonoscopy, virtual colonoscopy endoscopy, or arthroscopy. In addition, the acquired medical images may include completely virtual elements that have been graphically rendered in a virtual 3D space and added into the acquired medical image. This may include rendered tags, rendered anatomy (e.g., rendered bones, nerves, tendons, etc.), rendered orthopedic hardware to be installed, or other similar virtual renderings.

Figure 1E:
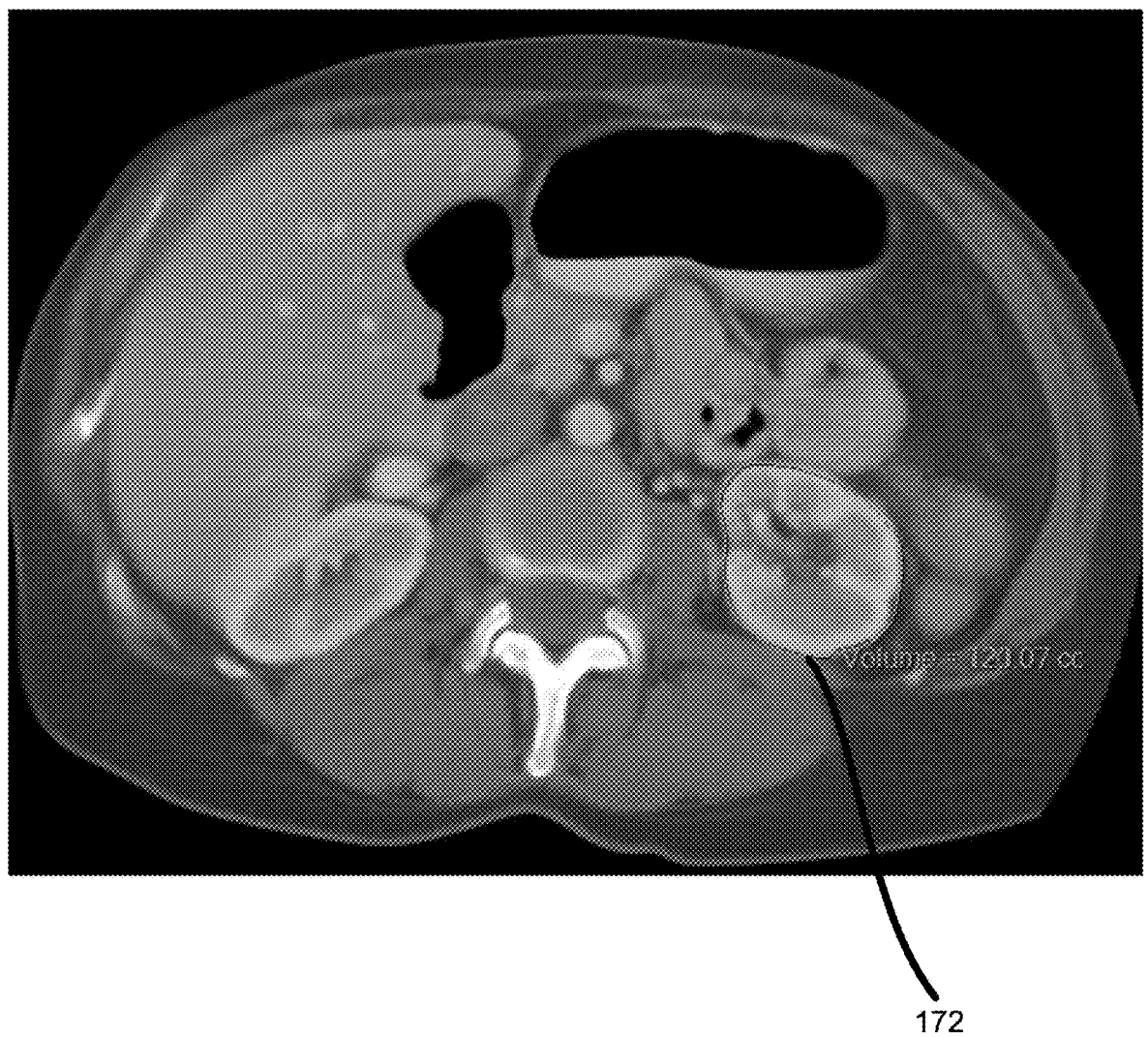
FIG. 1E illustrates a two dimensional augmentation tag for a kidney.

FIG. 1E illustrates a two dimensional (2D) augmentation tag for a kidney. In this case, a medical professional may annotate a 2D slice or layer of an acquired medical image to create an augmentation tag 172. The medical professional may notate the image by carefully outlining the kidney or by selecting a point in the center mass of the kidney tissue and requesting an application to find the boundary of the kidney. This 2D augmentation tag can be turned into a three dimensional (3D) augmentation tag is described in this disclosure. In an alternative configuration, FIG. 1E can illustrate a 2D cross-sectional view of a 3D augmentation tag.

Figure 1F:
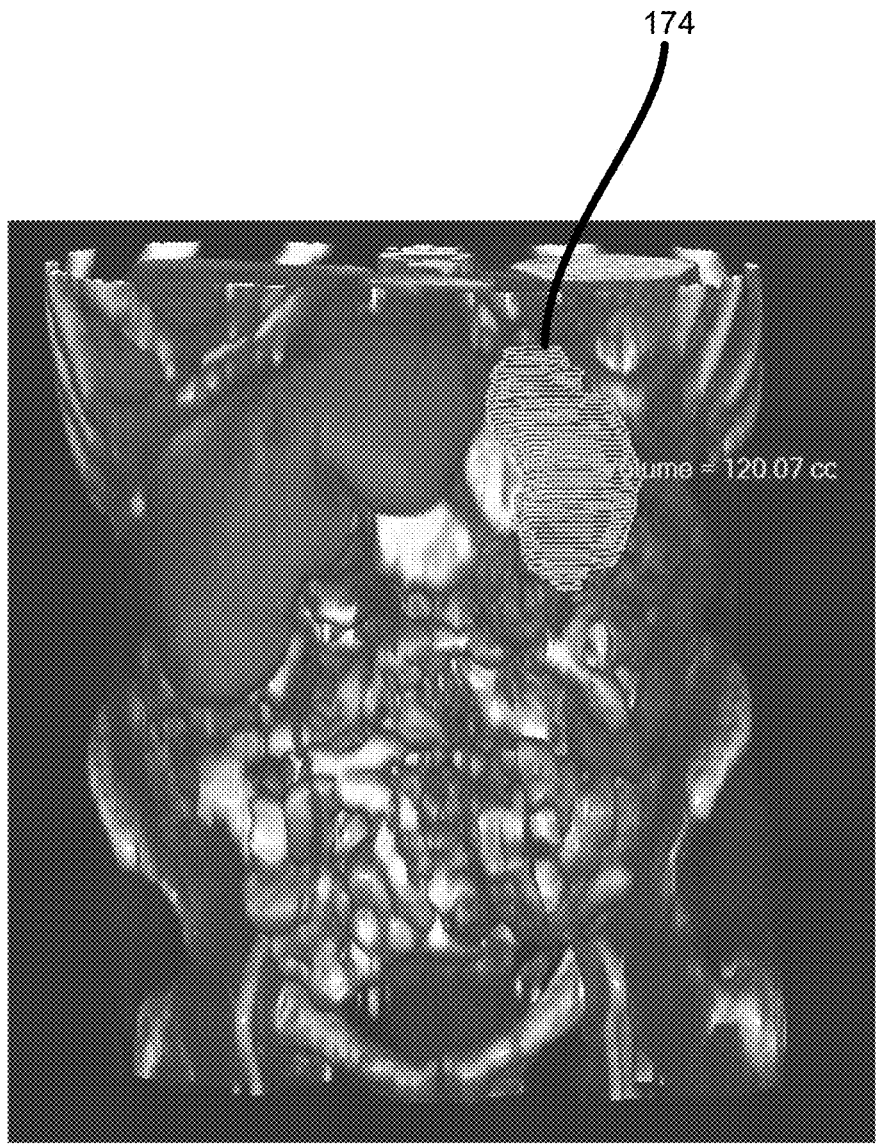
FIG. 1F illustrates a three dimensional augmentation tag for a kidney.

FIG. 1F further illustrates a three dimensional (3D) augmentation tag for a kidney 174. The 3D augmentation tag can be created by a medical professional requesting the application to take the 2D augmentation tag and find the entire kidney shape by identifying tissue similar to kidney tissue selected by a medical professional in the acquired medical image. Once the application has identified what is believed by the application to be the kidney, the medical professional may change the shape of the kidney to most accurately identify what needs to be addressed by a medical procedure. This may mean adjusting the augmentation tag to identify protrusions or areas that were not correctly captured by the application or excluding portions that are not desired to be in the augmentation tag. Alternatively, the medical professional can annotate the kidney entirely in 3D, if desired. The volume of the 3D augmentation tag can be computed in order to assist a medical professional with determining how large or small the anatomical structure.

Figure 1G:
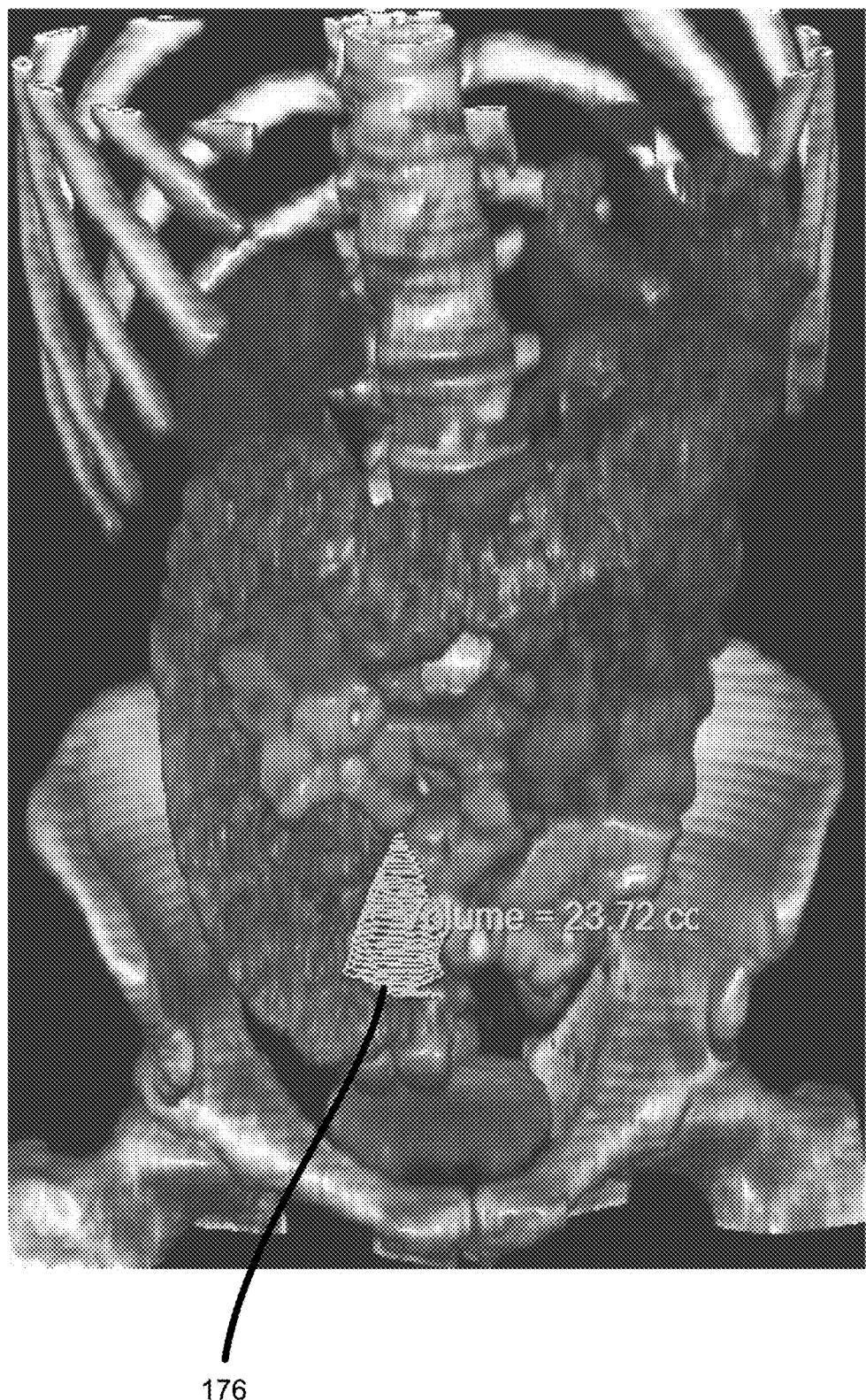
FIG. 1G illustrates a three dimensional augmentation tag for an abscess.
Figure 1H:
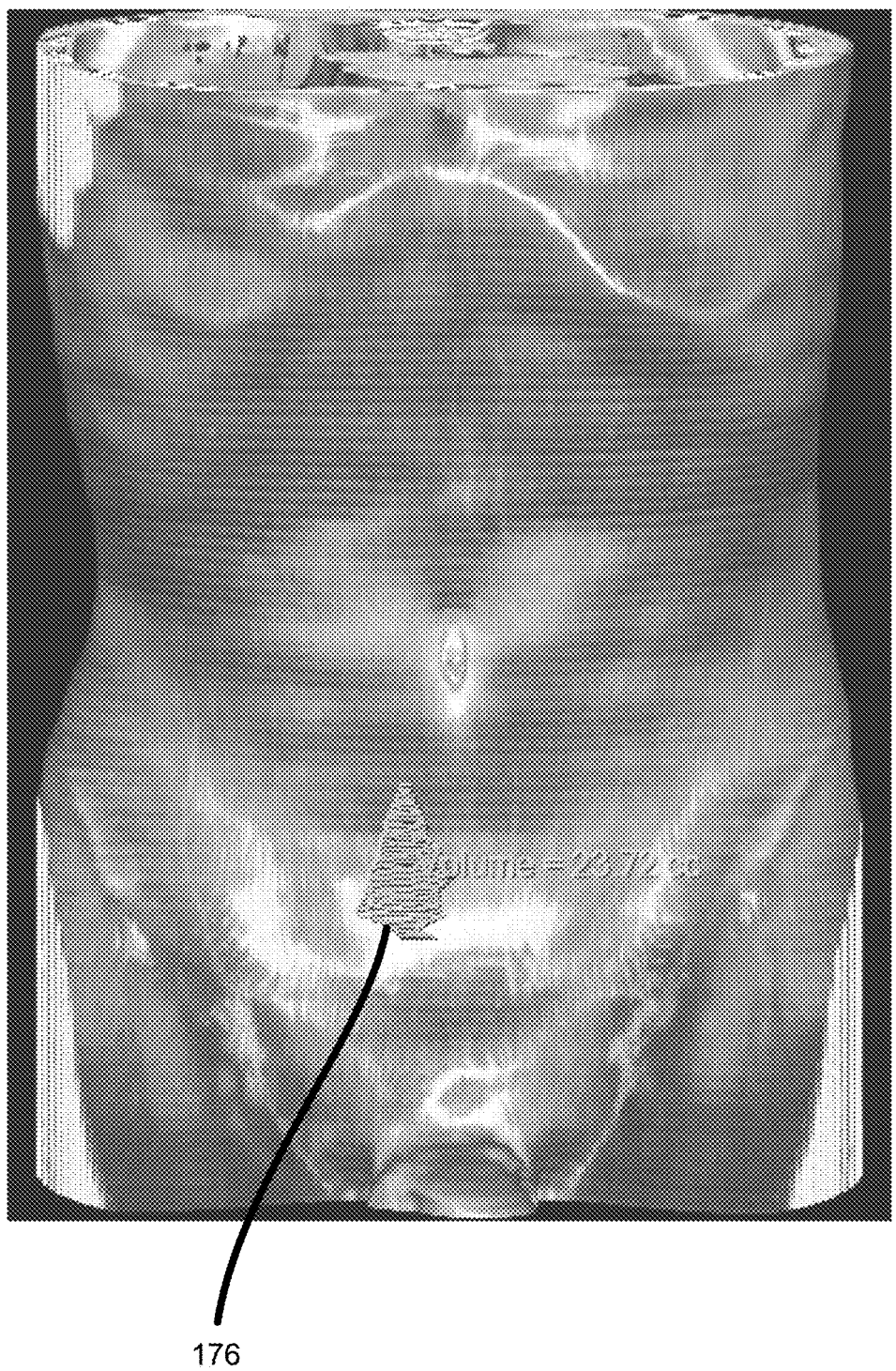
FIG. 1H illustrates a three dimensional augmentation tag for an abscess as covered by imaged skin.

FIG. 1G illustrates a three dimensional (3D) augmentation tag for an abscess 176 where the 3D augmentation tag is shown with the acquired medical image that depicts a bowel structure and bone structure of the patient, where the abscess is under the bowel structure. In the acquired medical image, the bowel structure may be turned on or off so that a medical professional can see the augmentation tag in various contexts (e.g. with or without bowels). FIG. 1H further illustrates a 3D augmentation tag for an abscess as covered by imaged skin. This view using the imaged skin can provide a different context for the medical professionals who may need to perform a medical procedure. As discussed, these acquired medical images with the augmentation tags can be used as overlays using an AR headset.

Figure 1I:
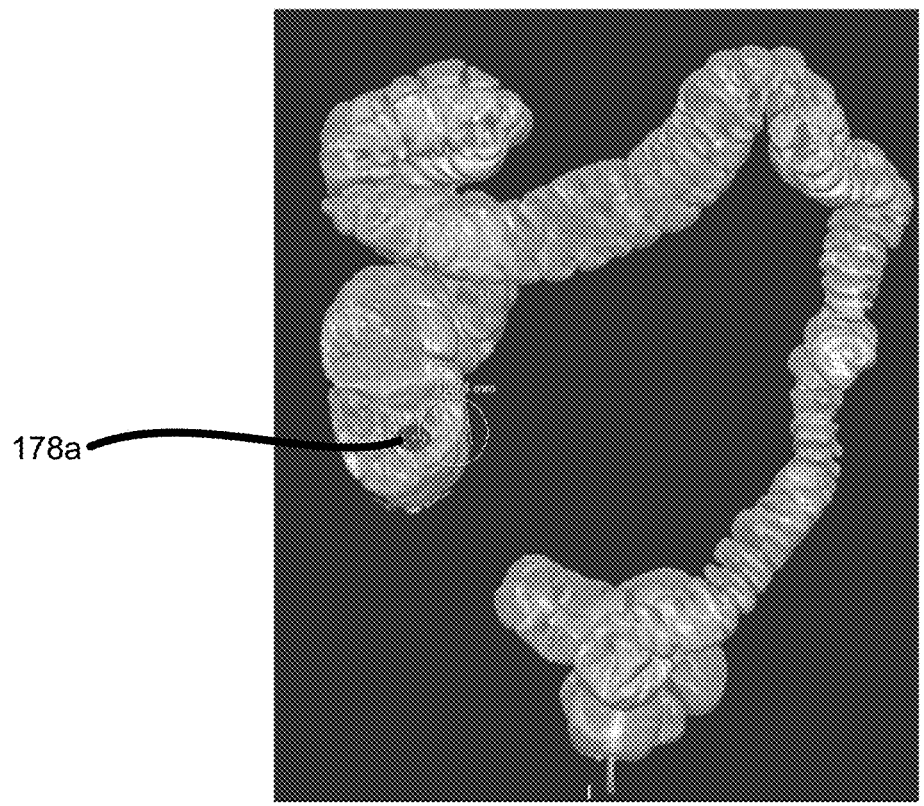
FIGS. 1I and 1J illustrate a three dimensional augmentation tag for an anatomical structure in a colon.
Figure 1J:
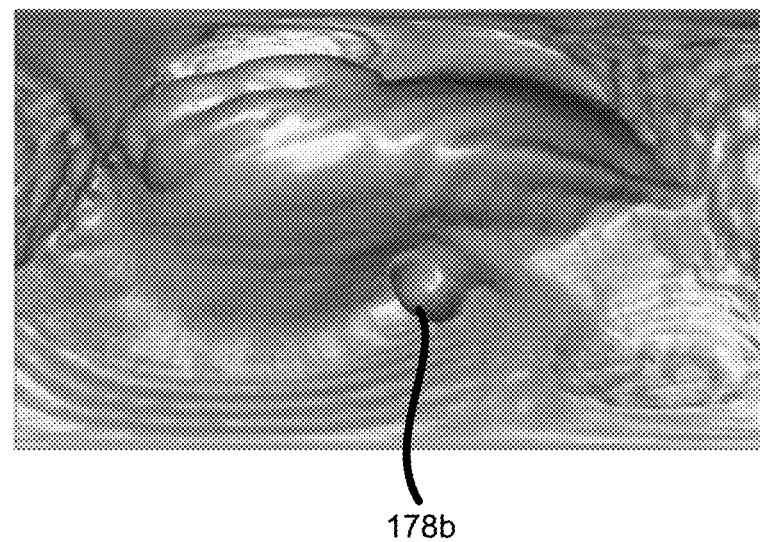

FIGS. 1I and 1J illustrate a 3D augmentation tag for an anatomical structure (e.g., a polyp or tumor) in a colon. The image of the colon may be created using neural network machine learning methods. Polyps or possible cancerous structures in the colon can be identified using neural network machine learning techniques. The neural networks may have been trained using a large number of medical training data cases to be able to find or classify the polyp. Alternatively, a medical professional can mark the polyp with an augmentation tag or use automatic assistance of an application to more easily mark the polyp.

Figure 2A:
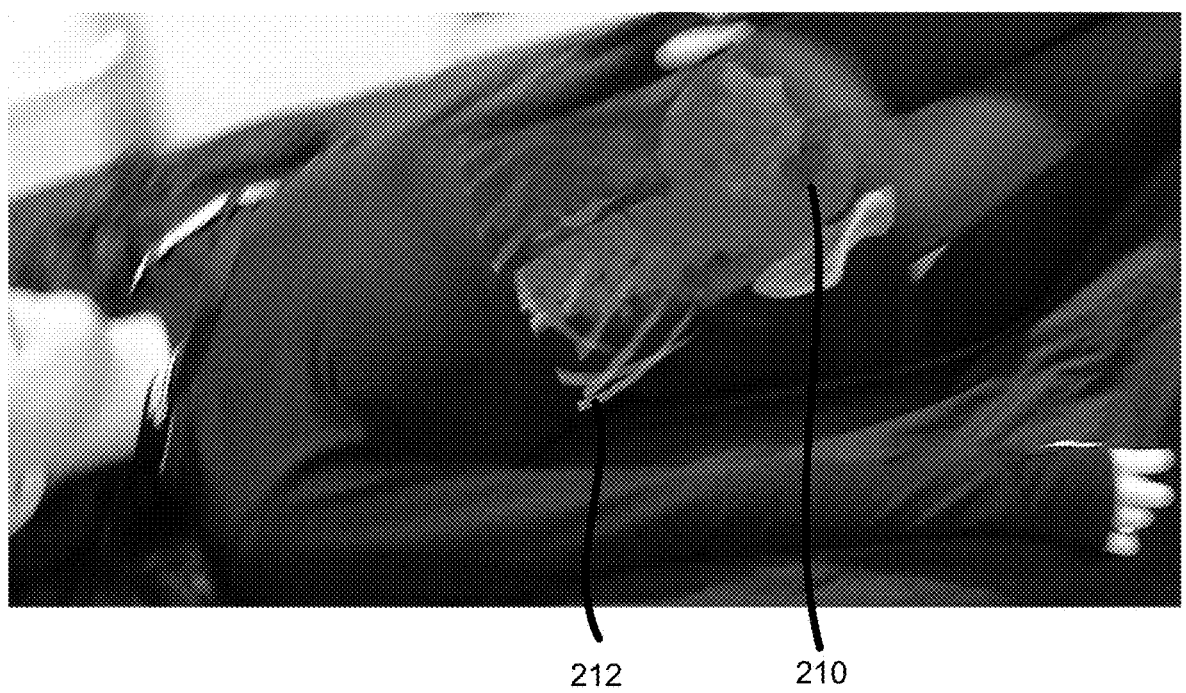
FIGS. 2A-2D illustrate an augmentation tag in an acquired medical image used as an overlay for an appendix.
Figure 2B:
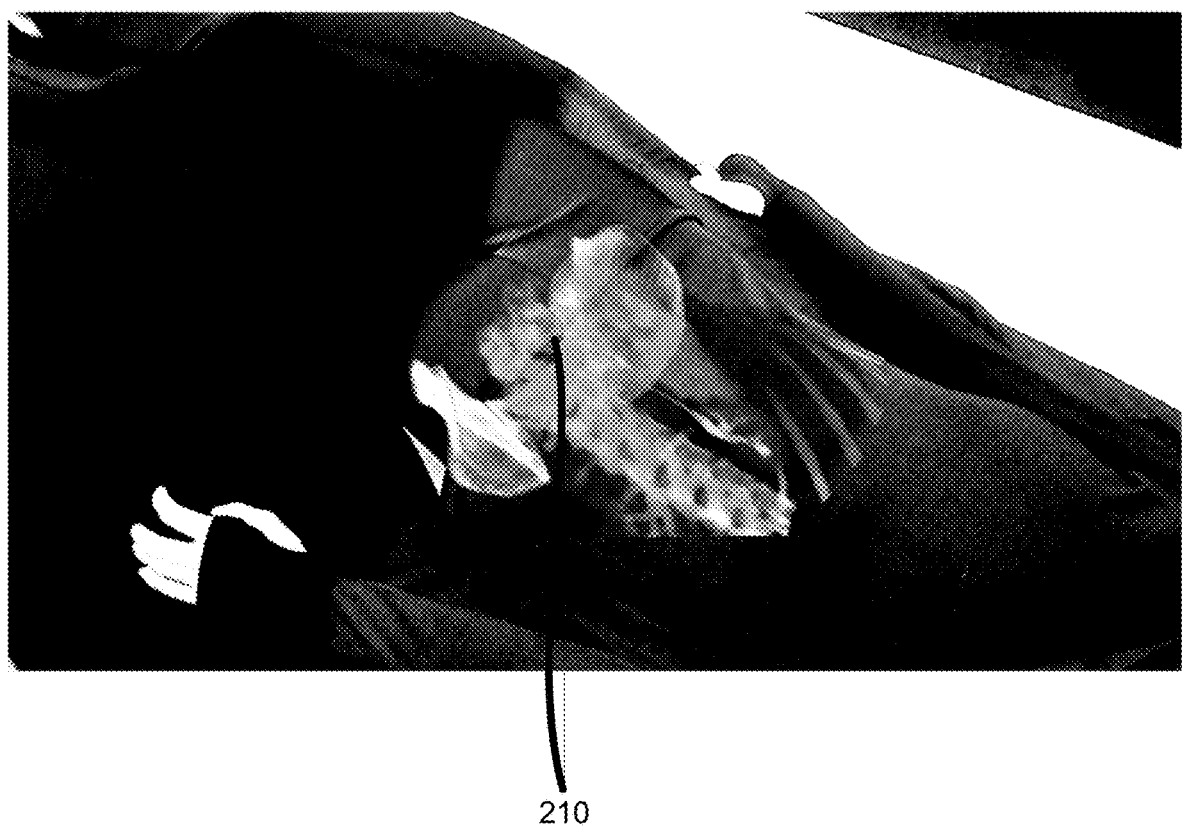
Figure 2C:
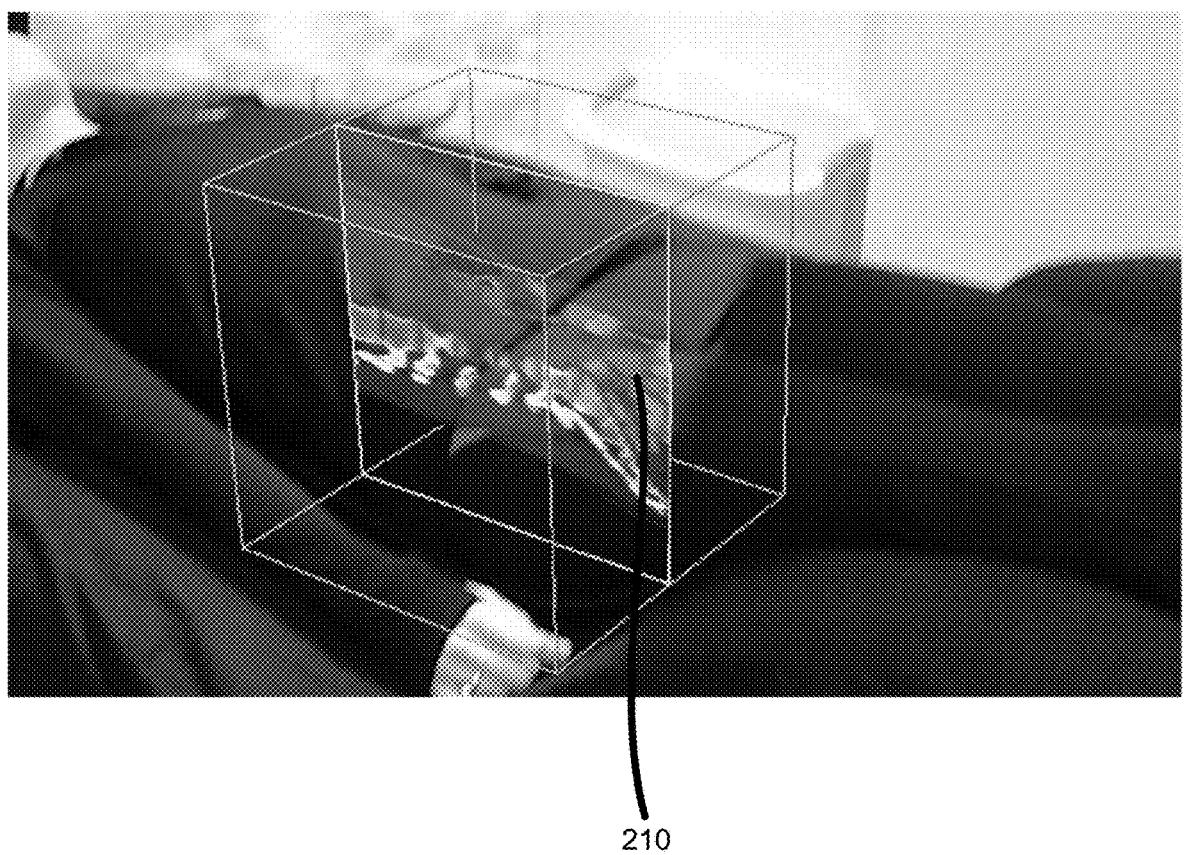
Figure 2D:
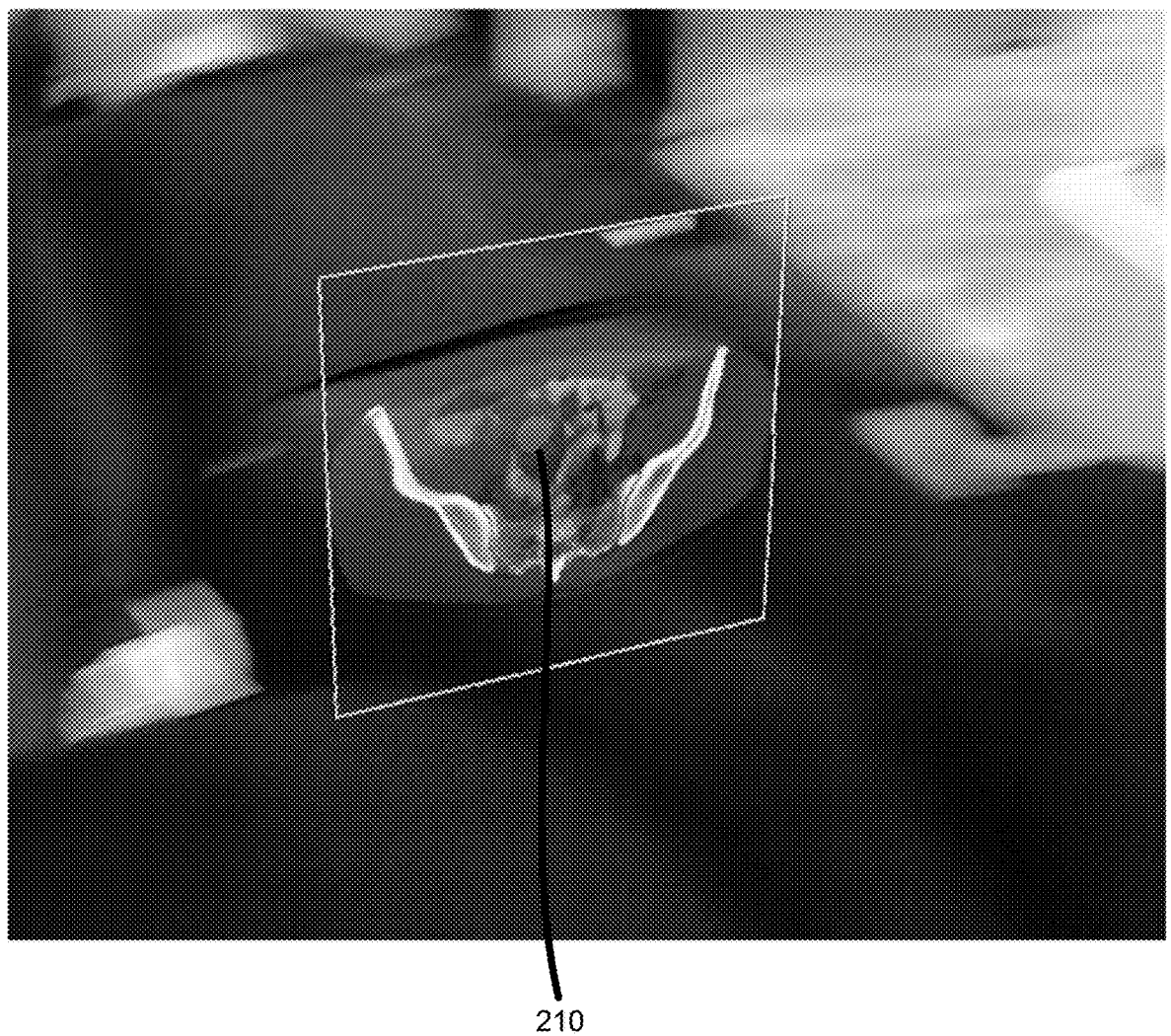

FIG. 2A illustrates an augmentation tag 210 and an acquired medical image 212 used as an overlay with an AR headset for an appendix related medical procedure. The augmentation tag 210 and acquired medical image 212 are viewed from a right side of a patient. The acquired medical image 212 also illustrates skeletal structure and other patient organs. While the augmentation tag is illustrated in this figure as darkened semi-spherical structure (or in some related figures as a lighter structure), other augmentation tags may be used that are colored (e.g., green, red, blue, etc.) or textured (e.g., special graphical textures such as hatching, striping, or other textures). FIG. 2B illustrates the same augmentation tag 210 and acquired medical image as viewed from the left side of the patient. FIG. 2C illustrates an augmentation tag 210 for the appendix as viewed from the right side of a patient and an overlay from the acquired medical image that is a cross sectional view in a partial sagittal plane from the acquired medical image. FIG. 3D illustrates an augmentation tag 210 and an acquired medical image that is a cross sectional view in a transverse plane for the acquired medical image.

Figure 3A:
FIG. 3A illustrates an acquired medical image that is overlaid on a patient's head and depicts a cross section of the patient's neck.

FIG. 3A illustrates the use of an augmented reality headset where an acquired medical image for a patient's head and brain is anchored to the real world view of the patient's head. As can be seen in the image, a cross section of the patient's brain is visible in the overlay on the patient's head and neck and medical personal can view anatomical structure of the patient prior to any invasive action on the part of the medical professionals.

Figure 3B:
FIG. 3B illustrates an acquired medical image that is overlaid on a patient's head region and illustrates that hand gestures may be used to control the augmented reality headset.

FIG. 3B illustrates that hand gestures may be in front of the AR headset in order to control the AR headset. For example, zooming or shrinking motions can be made by opening and closing a hand. Similarly, moving through multiple layers of the acquired medical image can be performed by pinching each side of the acquired medical image and simultaneously moving hands up or down.

This technology may use augmented reality (AR) headsets, virtual reality VR headsets, transparent overlay systems that are not worn on the head, or other types of mixed reality systems that are available or may become available. To further help explain this technology, an example of an AR headset will be described now. However, the use of this technology is not limited to only AR headsets but may use other types of augmented reality or mixed reality systems. An example AR headset may have a thick visor-like band that wraps around the head of medical professionals. The visor may be lightweight and adjustable to fit different head sizes. In some configurations, the AR headset may be wirelessly networked and provide audio output. Alternatively, medical professionals may wear the AR headset like corrective glasses and the processor portion of the AR headset may be worn on around a person's waist, or attached to a separate processing station.

The AR headset may include holographic lenses and a depth camera as well as speakers above the ears and an on-board processor with at least one GPU (graphics processing unit). The headset may also include venting to keep the headset from overheating. The wireless connection may be Bluetooth, Wi-Fi, ZigBee, cellular, or another type of wireless connection.

Additional support sensors may be included in an AR headset such as an ambient light sensor and multiple environment sensing cameras that work in combination with a depth sensing camera to identify a work space within which the augmented reality environment can be created.

A high definition camera may also be included in an AR headset to take photos and record mixed reality video. Multiple microphones may be included to capture local audio. The AR headset may include a re-chargeable battery system or the AR headset may receive power from an adapter in a laptop fashion.

Some AR headsets may be controlled by gestures, voice or a remote controller and such controls may be used to control objects or interfaces of the AR headsets. Hand gestures may also be made in front of the AR headset and may be captured by one or more of the front facing cameras. In addition, a pointer device, such as a mouse, stylus, clicker or other pointer devices may be used to control the AR headset.

The depth camera may be low power and may have a field of view of 60 degrees in the X axis and 60 degrees in the Y axis, for example. Other fields of view for a depth camera can be used. There may be multiple cameras around the headset (i.e., on the front and sides). These cameras can capture video of the physical surroundings, track the user's hands to identify gestures, and help to track head movements along with motion sensors on the AR headset.

The ability to blend acquired medical images, virtual models, and augmentation tags with a live environment means that the lenses may be transparent. In one configuration that may be two lenses, one for each eye, and the lenses may be made up of three layers of glass (blue, green and red). A projection engine or light engine above the lenses may project light into the headset and tiny corrugated grooves in each layer of glass diffract these light particles, making the light bounce around to enhance the illusion of perceiving virtual objects at virtual distances. These images may appear as what may be called holograms. Once the AR headset has mapped a room, the virtual images can be blended into the real environment viewed through the semi-transparent lenses.

The AR headset can anchor or "pin" virtual images or objects into place with respect to the real environment or room. Once a virtual object or virtual image is locked in place for the viewable environment or real environment, then a user can move around the virtual object or virtual image to view the virtual object from different angles without the object or overlay image moving.

Figure 4:
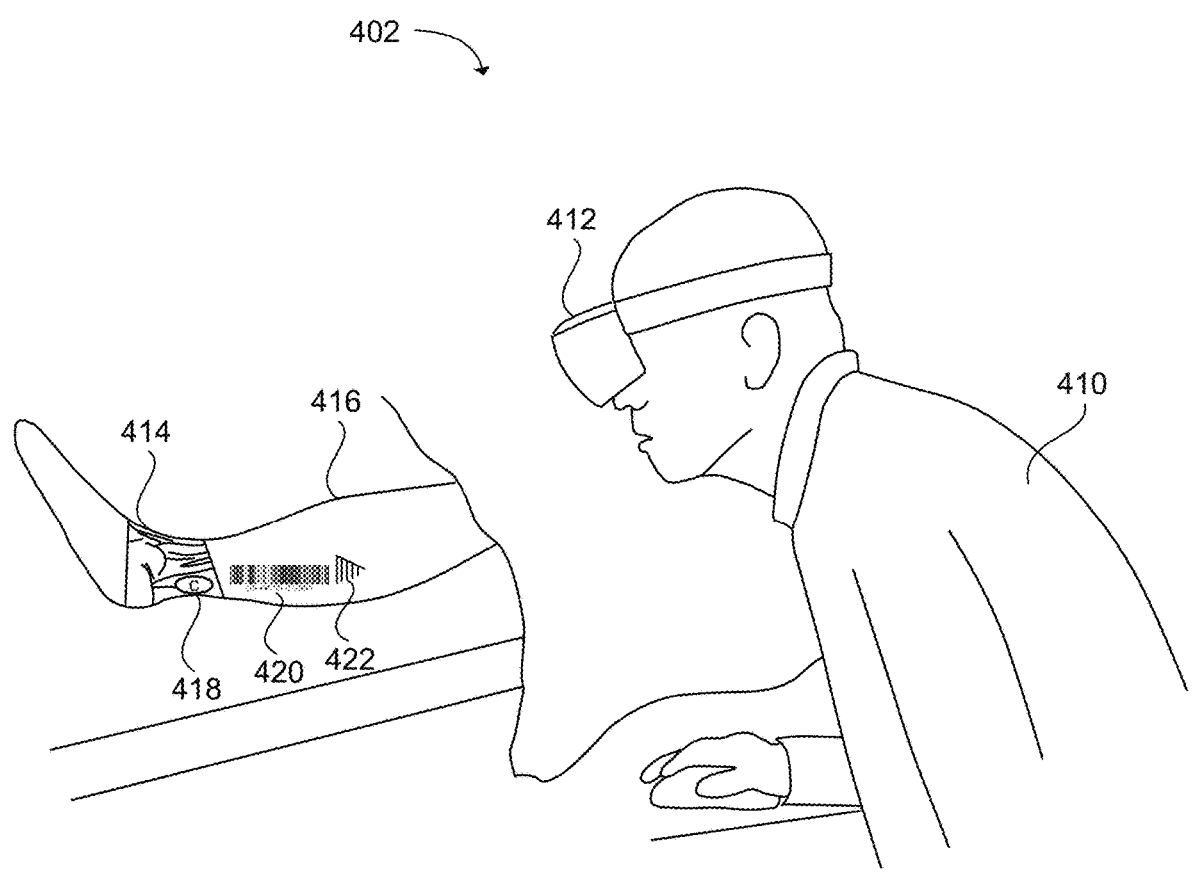
FIG. 4 is an illustration of an example use of an augmented reality head set to augment a medical procedure using physical patient identifiers.

FIG. 4 illustrates the augmentation of a view of a medical procedure 402 for medical professionals 410 using an AR headset 412. A live image of patient anatomy and the surrounding environment or room may be obtained using a live image camera of the AR headset 412. A patient marker 420 that is located on the patient and can be identified in the image or video of the patient anatomy as obtained by the AR headset. The patient marker 420 may include information identifying the patient, anatomy to be operated upon, a patient orientation marker 422, and/or an image inversion prevention tag 422. The patient orientation marker 422 and the image inversion prevention tag 422 may be separate or combined into one marker or tag with each other or the patient marker 420.

A visually scannable symbol attached to a patient, such as a barcode, can provide information to retrieve the identity of the patient and to retrieve an associated acquired medical image 414 or multiple associated acquired images. The patient orientation marker 422 can be used to ensure that the acquired medical image is oriented correctly with respect to the patient anatomy. The patient marker 420 and an image orientation marker 422 in the radiological image may be matched with markers in the acquired medical image to enable matching orientation of the acquired medical image with the patient orientation marker 422 on the patient anatomy. This avoids orientation or calibration errors when the acquired medical image 414 is aligned with the patient anatomy. The image inversion tag 422 can be used to make sure the image is not inverted or flipped over when the alignment occurs.

In one configuration of the technology, a bar code, QR code, or special marker may be used to mark the right patient for the medical procedure, mark right side of the patient, or mark the right appendage on which to perform a medical procedure. The optically scannable code or marker on the patient's anatomy can also be compared the patient data associated with the acquired medical image to see if the patient's acquired medical image and/or anatomy matches with the patient marker 420 provided.

An acquired medical image 414 can be associated with the patient anatomy 416 based in part on the patient marker 420. This means that the correct acquired medical image 414 can be retrieved based on the patient identity and the anatomy to be operated on, as identified in advance. The acquired medical image 414 can be anchored or fixed to the patient anatomy based in part on the patient orientation marker 422 or image inversion prevention tag 422. Alternatively, the acquired medical image 414 can be overlaid onto the patient anatomy by identifying the topological structure of the patient anatomy 416. Automating this process can reduce errors, and vastly reduce expensive operating room time.

An augmentation tag 418 associated with the patient marker 420 and a location in the acquired medical image or radiological image can also be retrieved for enabling viewing of an augmentation tag 418 overlaid onto the patient's anatomy 416. The acquired medical image 414 and the augmentation tag 418 can be projected onto lenses in an augmented reality headset 412 to form a single graphical view which is virtually overlaid onto the patient anatomy being viewed.

In one configuration, an endoscopic video feed may be combined into the single graphic view. An augmentation tag can also be used to identify a size and shape of 3D structures in the endoscopic video feed and to identify where an endoscope is estimated to be located in the patient anatomy.

Figure 5:
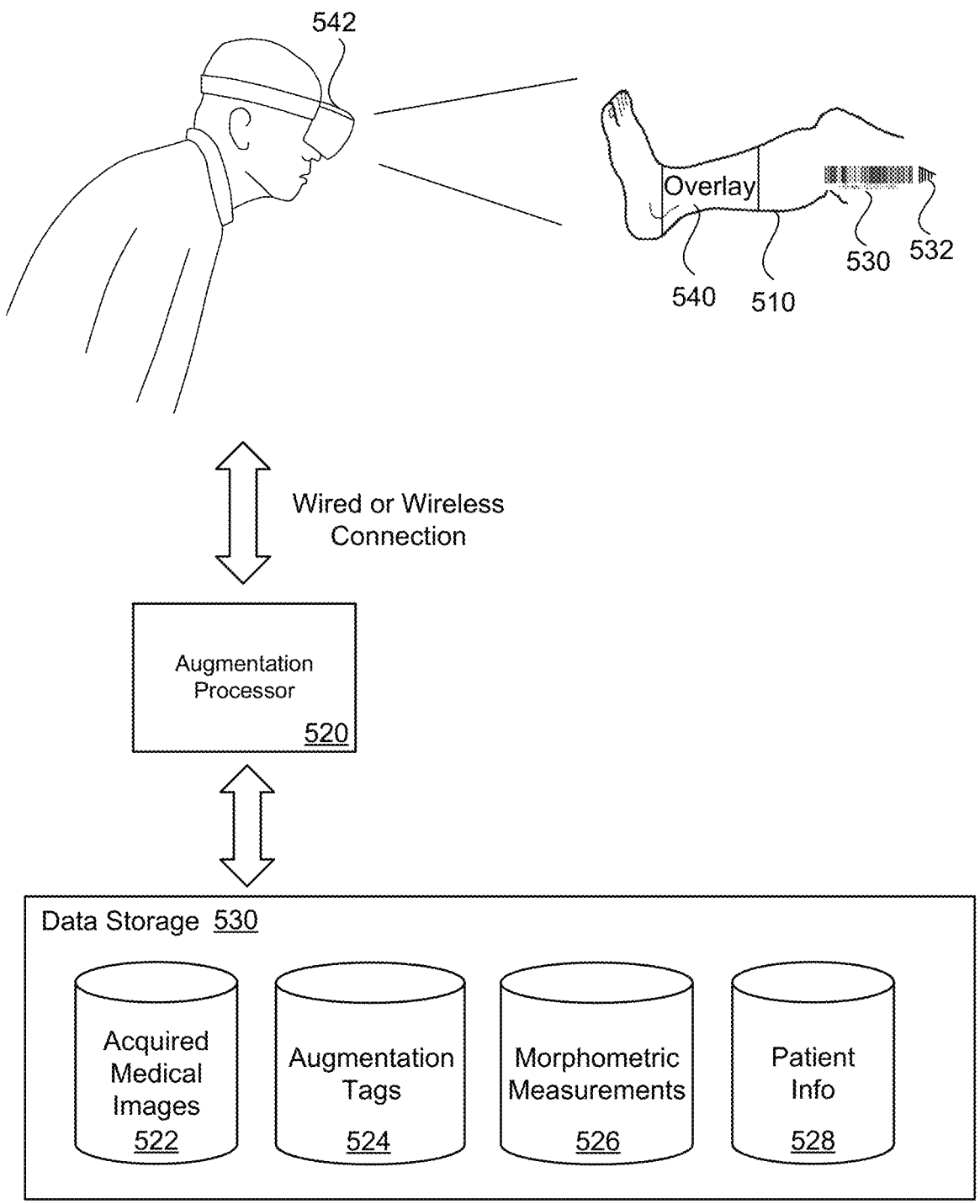
FIG. 5 is a block diagram illustrating an example of a system for augmenting a view of a medical procedure using data pulled from data storage.

FIG. 5 illustrates a system for augmenting a view of a medical procedure, such as a surgical procedure. The system may include a camera in an AR headset 542 or a camera associated with the system, and the camera may be configured to obtain a live image of patient anatomy 510. The camera may provide a live video feed of viewable patient anatomy for analysis by the AR headset 542. The video may be analyzed to identify environment orientation cues such as appendage locations, edge detection, depth detection, or features in the video images captured. In addition, the live video may be recorded or otherwise streamed to another location.

An augmentation processor 520 in the system can be configured to measure or define morphometric measurements of patient anatomy 510 as captured by the camera. The morphometric measurements may be metrics about the patient's anatomy, such as: shape, width, height, depth and contour of an appendage or patient anatomy. These morphometric measurements may be relative measurements or absolute measurements where a reference object or measurement key is provided. The augmented reality system can map the external contours of the patient using the depth camera or distance ranging cameras and can create a polygonal mesh that can be compared to the surface layer of the patient's 3D data obtained with imaging techniques. Thus both the "virtual" and "real" data can be compared for a match much like a finger print in 3D.

The augmentation processor 520 may determine whether the morphometric measurements measured from live video or images match pre-measured morphometric measurements associated with the patient anatomy as retrieved using the patient marker 530. For example, a patient's leg as presented in person may have certain measurements for length, width, height, shape or other morphmetric measures that can be matched to pre-measured morphometric measurements.

An acquired medical image 524 associated with the patient anatomy can then be retrieved as defined by the patient marker 530 and the patient anatomy 510. The acquired medical image 540 can be aligned with the patient anatomy 510 using the morphometric measurements and confirmed morphometric measurements.

The system may include an AR headset 542 that is configured to project the acquired medical image 522 and the augmentation tag(s) 524 onto semi-transparent lenses in the AR headset to form a single graphical view which is overlaid 540 on the patient anatomy being viewed by the user or medical professional using the AR headset. For example, a similar image may be projected into each eye, which may enable a 3D (three dimensional) viewing effect.

A notification can also be provided to the doctor or medical professional that the acquired medical image matches the patient anatomy as defined by the morphometric measurements. This way the doctor can be assured that the right patient and correct physical structure (correct leg or arm, etc.) is being operated upon with the correct acquired medical image 522. Not only is the patient's identity being checked by a patient marker but information or images retrieved can be checked using a comparison of the real patient anatomy being view in the real world as compared the morphometric measurements previously made. When a match is confirmed, this increases the chances the medical procedure will be accurate or correct.

In the case, where the morphometric measurements from the patient in the medical procedure do not match with the previously collected morphometric measurements associated with the patient identifier, then then a warning or error can be presented to the doctor or medical professionals. If a matching error does occur, the doctor may determine what information needs to be checked further and whether to proceed with the medical procedure or to terminate the medical procedure. This confirmation may be especially important where the patient is under sedation and cannot communicate with the attending medical professionals.

The morphometric analysis or capture for the patient's anatomy during imaging to identify a medical problem, and then the checking of the morphometric data upon treatment of the problem can result in more accurate patient treatment and avoid possible errors. As a result, this technology may perform a morphometric memorization of the patient or of anatomical aspects of the patient that are desired to be recorded. Then a graphical warning can be provided to medical professionals, if the morphometric comparison of the pre-captured anatomical structure and the anatomical structure currently viewed using the AR headset during a medical procedure does not match.

For example, if a doctor is going to operate on a patient's skull and the doctor needs to put a burr hole in the skull, then the doctor can have the augmented reality surgery system check the patient to make sure the shape of that patient's skull in the medical procedure matches the same shape as the information in the acquired medical image that was previously captured during a diagnosis phase. If the shape of the skull is not the same, a warning can be flashed to the doctor or medical personnel. Certain metrics for anatomical structure, such as the size, shape, amount of fat, facial details and similar skull details can be checked against morphometric data stored that previously measured these details for the patient.

In the context of morphometric analysis, a marking system with a bar code can be scanned to identify the patient. For example, an ID band may be scanned and the ID information may activate a download of the patient's acquired medical images and morphometric data because of the bar code. The acquisition of the patients acquired medical images with morphometric data associated with the acquired medical images can then be checked against the morphometric data computed from the live images or medical procedure images being captured from the patient using the AR headset. Once the patient identity has been confirmed using morphometry, then augmented tags may be loaded and combined with the acquired medical image. Finally, the surgeon may begin a medical procedure on the patient because the patient identity, acquired medical image, morphometry and similar aspects of the surgery have been verified.

The patient marker 530, as discussed above, may be identified in the image of the patient anatomy 510 and the patient marker 530 may include information identifying the patient and pre-measured morphometric measurements 526 stored in a database. The patient marker 530 may be a scannable symbol including at least one of: a 1D (one dimensional) bar code, a 2D (two dimensional) bar code, a picture, an image, a custom generated geometric shape, or a RFID (radio frequency ID) and information from the patient marker 530 may be used to retrieve the identity of the patient, patient information 528, and to retrieve the acquired medical image 522. In a more specific examples, the patient marker 530 may have a database key or value used to look-up or query for the pre-measured morphometric measurements 526 stored in separate database. When the patient identity has been obtained using visual scanning, a bracelet, RFID or morphmetry, then an acquired medical image 522 matching the patient identity and other patient information may be loaded along with augmentation tags that match the identity and the acquired medical image. These augmentation tags may be loaded, oriented based on the identity of the patient determined with the identity tag and/or morphometry.

The system may also retrieve an augmentation tag associated with a patient orientation marker 532 and a location (e.g., a Cartesian coordinate or another relative coordinate in the acquired medical image) in the acquired medical image or radiological image. The images of the acquired medical image and the augmentation tag may be combined into a single view using the patient marker and location. In addition, the patient orientation marker 532 may be used or matched with an image orientation tag in the acquired medical image or radiological image to orient the acquired medical image correctly over the patient's anatomy.

The system that includes the augmentation processor may also perform an operation identifying an image inversion prevention tag 532. An acquired medical image and patient anatomy can be aligned (e.g., rotated, flipped or inverted) using an image inversion prevention tag to ensure the acquired medical image is oriented correctly with respect to the patient anatomy.

In an alternative example of the present system, the headset may be a virtual reality (VR) headset, into which a video feed of a patient and operating room is fed and the acquired medical image can be composited together with the video feed. In this case the VR headset may not be transparent but the VR headset may enable the composited image to be used for diagnostic or other treatment purposes.

In one example, morphometry can be used to identify procedure road markers during a medical procedure such as endoscopy, arthroscopy, laproscopy, etc. For example, in a colonoscopy, certain uniquely shaped anatomical structures may be marked prior to the medical procedure. These anatomical structures may be marked using augmentation tags. In a specific example, 5 structures may be marked as road markers or milestones in the medical procedure. As the actual medical procedure progresses, the system may match one of the 5 structures viewed through a camera image and show a surgeon where the scope of the surgeon is located in the patient anatomy based on seeing a physical object that matches a virtual object that has already been recorded using morphometry. This location can be displayed as an overlay to the patient anatomy or in combination with the acquired medical image. This matching may proceed until all 5 structures have been identified during the course of the procedure.

In the case of a colonoscopy, many repeating structures exist and so if the unusual structures have been tagged in advance, then when the video feed from the colonoscopy has a match for an anatomical structure that has been previously tagged, the system can provide the surgeon or medical professionals doing the colonoscopy with an estimated position for where the endoscope is in the colon. This type of estimation can similarly apply to other types of scope style surgeries that might occur in the abdomen, joints, lungs, other portions of the gastric system (e.g., small intestine or stomach), reproductive organs, ureter, the respiratory system, etc. This technology can show where the scope or related procedure instruments are in the acquired medical image (MRI, CT scan) or in a virtual image based on a distance traveled or a matched anatomical structure in the acquired medical image.

The system can also provide a multi-feed display. The visual output for medical professionals can display: 1) an image of the visible skin (as captured by the visible light camera), 2) an image or video from a scope, 3) a virtual rendered image (CGI or computer generated image), 4) augmentation tags, and/or 5) an acquired medical image (e.g., the X-ray, MRI, or CT image). This allows medical personal to see multiple images on a single screen instead of multiple screens (e.g., one for the MRI, one on the scope device, one for the medical chart, etc.). This also enables medical professionals to switch between different data views.

As referred to herein, a "medical professional" may include physicians, physician assistants, nurse medical professionals, medical specialists, and any of a variety of other types of health care professionals.

As referred to herein, a "medical procedure" may include the science or practice of the diagnosis, treatment, and prevention of disease. A medical procedure may encompass a variety of health care practices intended to maintain and/or restore health by the prevention and treatment of illness in human beings. A medical procedure may also apply to tasks relating to health science, biomedical research, and medical technology to diagnose and treat injury and disease, such as through medication or surgery, as well as through therapies such as psychotherapy, traction, prostheses, biologics, ionizing radiation and so forth.

While the present technology is described in terms of medicine, the technology may alternately be applied in other areas of technology, science, etc. in which productivity is measured, such as according to a type of unit indicative of time, effort, skill, and so forth involved in completing a task.

Figure 6:
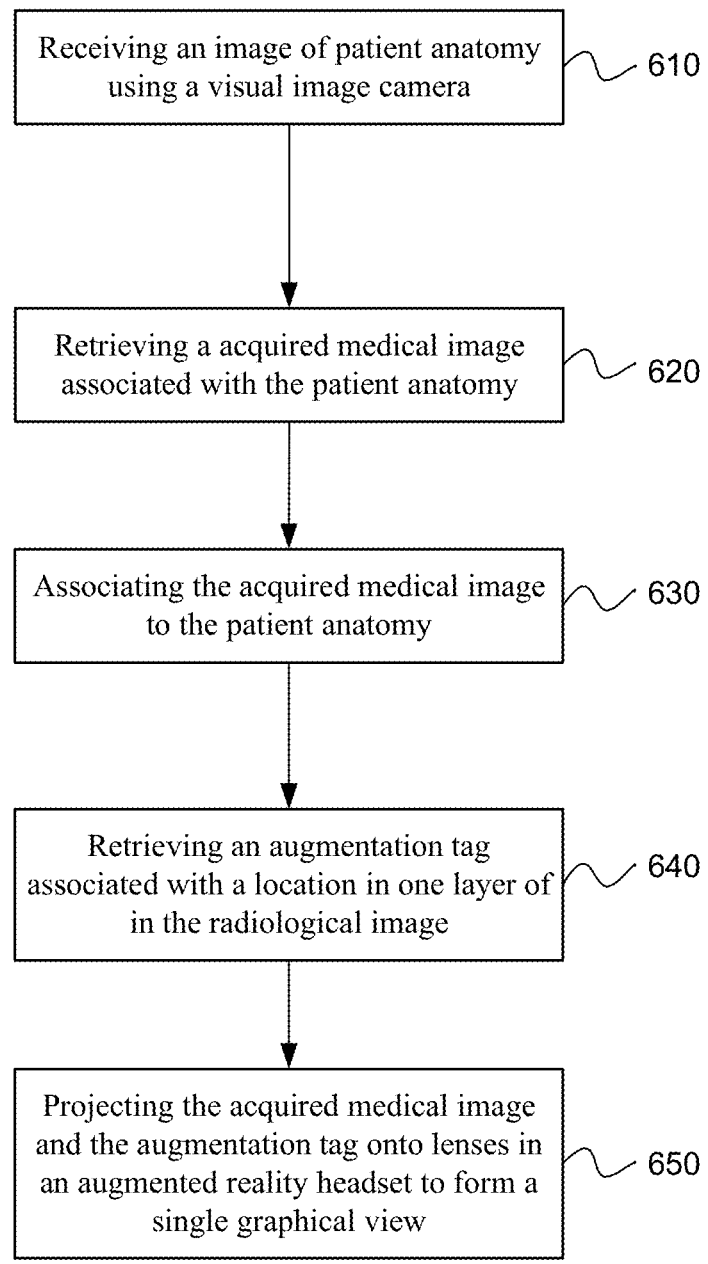
FIGS. 6 and 7 are flow charts illustrating methods for augmenting a view of a medical procedure.

FIG. 6 is a flow chart illustrating a method for augmenting medical imaging for use in a medical procedure. The method may include receiving an image of patient anatomy using a visual image camera, as in block 610. The image of the patient anatomy may be collected when the patient is having a medical procedure performed. An acquired medical image associated with the patient anatomy may then be retrieved, as in block 620. An example of an acquired medical image may be an MM, fMRI or CT scan.

The acquired medical image may then be associated with the patient anatomy, as in block 630. This association may be anchoring or fixing of the acquired medical image to a reference point on the patient's anatomy that matches the same anatomical point in the acquired medical image. An augmentation tag associated with a location in one layer of the acquired medical image can then be retrieved, as in block 640. This augmentation tag may represent an anatomical structure, a point where an incision may be made, or other mappings and markings for the medical procedure. The acquired medical image and the augmentation tag can be projected onto lenses in an augmented reality headset to form a single graphical view, as in block 650.

Figure 7:
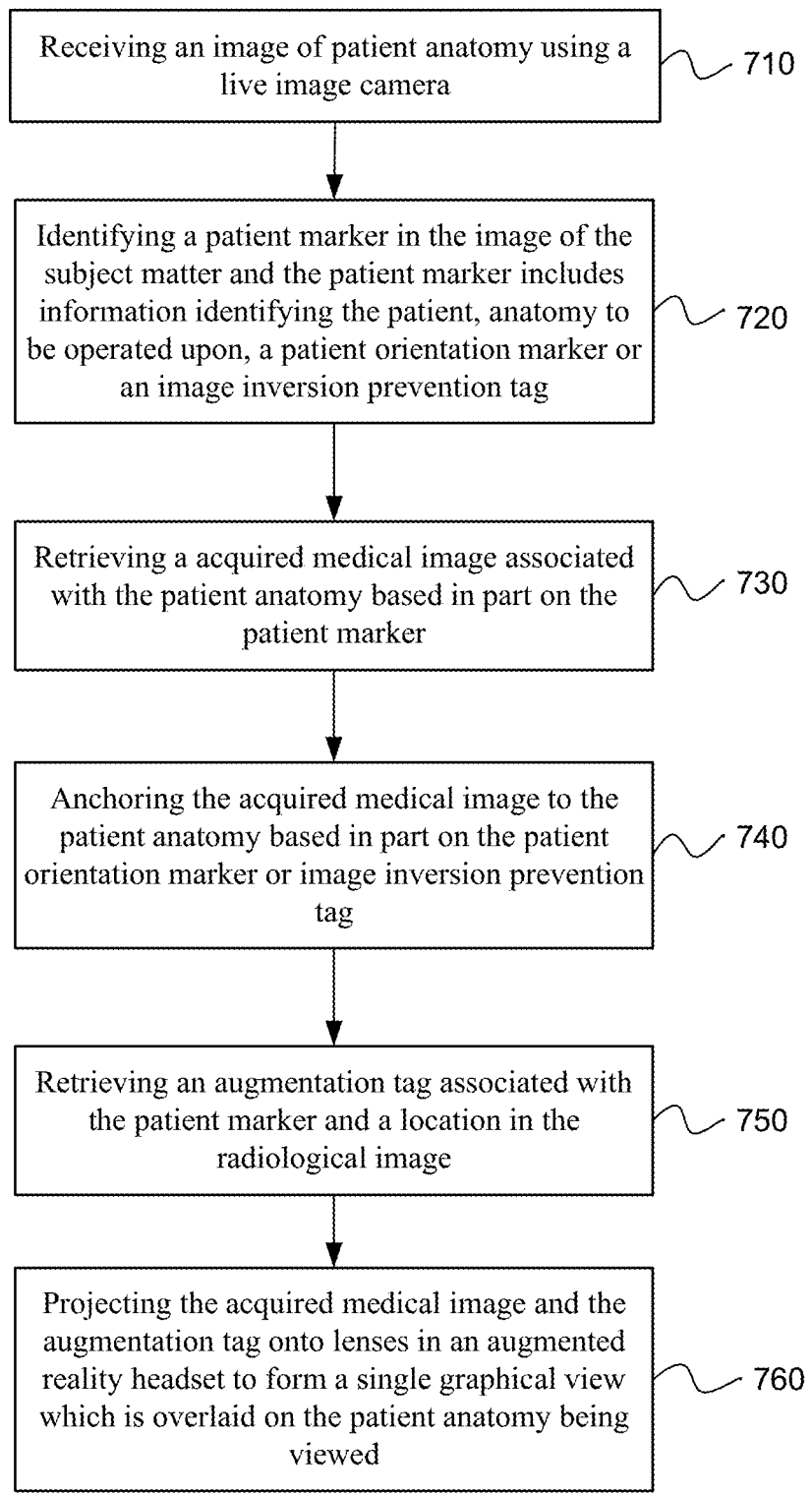

FIG. 7 is a flow chart illustrating a method to augment a view of a medical procedure. The method may include receiving an image of patient anatomy using a live image camera, as in block 710. This may be an image of a patient after a medical procedure is underway. A patient marker in the image of the subject matter may be identified, as in block 720. The patient marker may include information identifying the patient, anatomy to be operated upon, a patient orientation marker or an image inversion prevention tag.

An acquired medical image associated with the patient anatomy may be retrieved based in part on the patient marker, as in block 730. The acquired medical image may be a radiological medical image, a computer rendered image, or another type of visual light image. The acquired medical image can be anchored to the patient anatomy based in part on the patient orientation marker, as in block 740.

An augmentation tag associated with the patient marker and a location in the radiological image may be retrieved, as in block 750. The acquired medical image and the augmentation tag may be projected onto lenses in an augmented reality headset to form a single graphical view which is overlaid on the patient anatomy being viewed, as in block 760.

Figure 8:
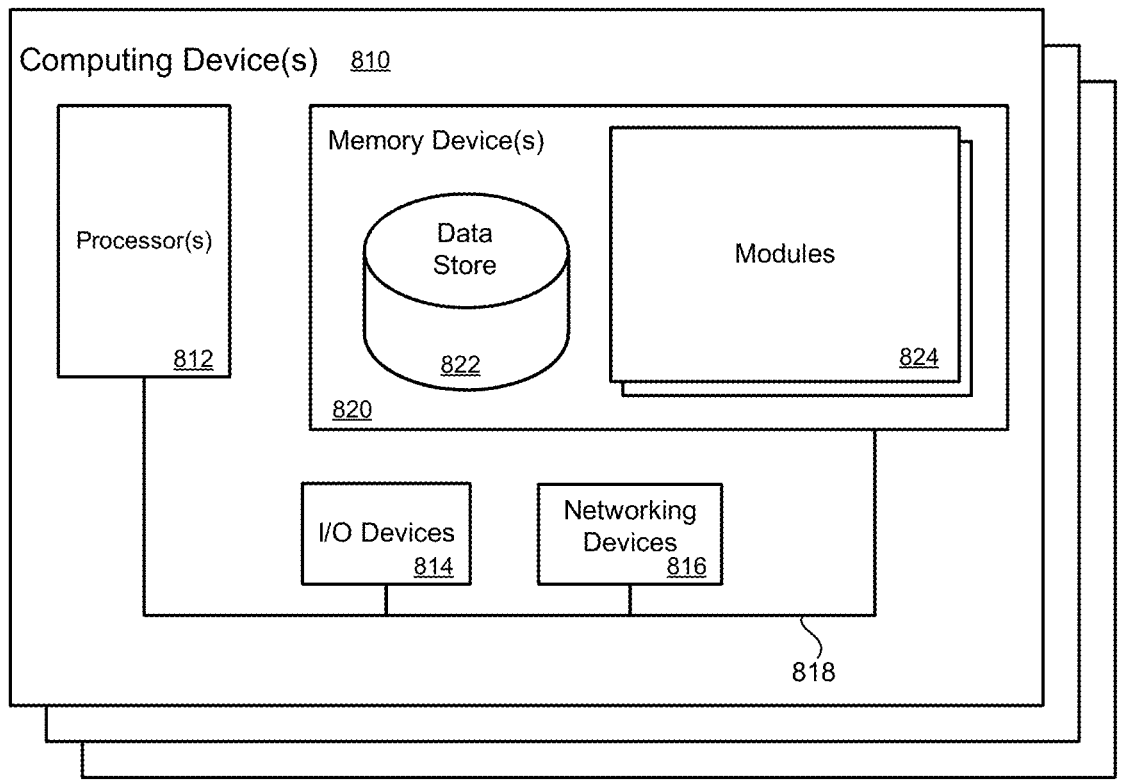
FIG. 8 is a block diagram that provides an example illustration of a computing device that may be employed in the present technology.

FIG. 8 illustrates a computing device 810 on which modules of this technology may execute. A computing device 810 is illustrated on which a high level example of the technology may be executed. The computing device 810 may include one or more processors 812 that are in communication with memory devices 820. The computing device may include a local communication interface 818 for the components in the computing device. For example, the local communication interface may be a local data bus and/or any related address or control busses as may be desired.

The memory device 820 may contain modules 824 that are executable by the processor(s) 812 and data for the modules 824. The modules 824 may execute the functions described earlier. A data store 822 may also be located in the memory device 820 for storing data related to the modules 824 and other applications along with an operating system that is executable by the processor(s) 812.

Other applications may also be stored in the memory device 820 and may be executable by the processor(s) 812. Components or modules discussed in this description that may be implemented in the form of software using high programming level languages that are compiled, interpreted or executed using a hybrid of the methods.

The computing device may also have access to I/O (input/output) devices 814 that are usable by the computing devices. An example of an I/O device is a display screen that is available to display output from the computing devices. Other known I/O device may be used with the computing device as desired. Networking devices 816 and similar communication devices may be included in the computing device. The networking devices 816 may be wired or wireless networking devices that connect to the internet, a LAN, WAN, or other computing network.

The components or modules that are shown as being stored in the memory device 820 may be executed by the processor 812. The term "executable" may mean a program file that is in a form that may be executed by a processor 812. For example, a program in a higher level language may be compiled into machine code in a format that may be loaded into a random access portion of the memory device 820 and executed by the processor 812, or source code may be loaded by another executable program and interpreted to generate instructions in a random access portion of the memory to be executed by a processor. The executable program may be stored in any portion or component of the memory device 820. For example, the memory device 820 may be random access memory (RAM), read only memory (ROM), flash memory, a solid state drive, memory card, a hard drive, optical disk, floppy disk, magnetic tape, or any other memory components.

The processor 812 may represent multiple processors and the memory 820 may represent multiple memory units that operate in parallel to the processing circuits. This may provide parallel processing channels for the processes and data in the system. The local interface 818 may be used as a network to facilitate communication between any of the multiple processors and multiple memories. The local interface 818 may use additional systems designed for coordinating communication such as load balancing, bulk data transfer, and similar systems.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A method for augmenting medical imaging of a patient, the medical imaging displayed using an augmented reality headset worn by a medical professional, the method comprising:
   retrieving an acquired medical image associated with patient anatomy from data storage, the acquired medical image comprising imaging acquired of one or more anatomical structures of the patient anatomy;
   aligning the acquired medical image with a portion of the patient anatomy viewable through augmented reality headset, wherein the one or more anatomical structures of the medical imaging are aligned with the patient anatomy;
   retrieving an augmentation tag from data storage, the augmentation tag associated with a location of the acquired medical image, wherein the augmentation tag identifies at least one anatomical structure of the acquired medical image found at the location; and
   projecting the acquired medical image and the augmentation tag using the augmented reality headset to form a single graphical view as an overlay to the patient anatomy viewable through a lens of the augmented reality headset.

2. The method as in claim 1, further wherein augmentation tag conforms to a three dimensional (3D) structure in the acquired medical image to identify an anatomical structure associated with a medical procedure to be performed.

3. The method as in claim 1, wherein a plurality of augmentation tags are provided in a plurality of layers of the acquired medical image and the plurality of augmentation tags are associated to form a tag group to guide a surgeon.

4. The method as in claim 1, further comprising:
   creating a plurality of two dimensional (2D) augmentation tags each located on one of a plurality of layers of the acquired medical image; and
   joining the plurality of 2D augmentation tags to form a three dimensional (3D) augmentation tag that extends through multiple layers of the acquired medical image.

5. The method as in claim 1, wherein retrieving an augmentation tag further comprises retrieving a plurality of augmentation tags that are linked together to represent an anatomical structure in independent layers of the acquired medical image.

6. The method as in claim 1, wherein retrieving an augmentation tag further comprises retrieving a plurality of augmentation tags that are linked together to show a surgical path of an incision through the patient anatomy with respect to the one or more anatomical structures through a plurality of layers of the acquired medical image.

7. The method as in claim 1, further comprising capturing the acquired medical image using a MRI, CT scan, X-ray, ultrasound, or photographic images internal to a human body.

8. A non-transitory machine readable storage medium having instructions embodied thereon, the instructions when executed cause a processor to augment medical imaging of a patient during a medical procedure using an augmented reality headset worn by a medical professional during the medical procedure, comprising:
   identifying a patient marker on patient anatomy viewable through the augmented reality headset, the patient marker comprising information identifying the patient, information identifying patient anatomy that is a subject of the medical procedure, a patient orientation marker, or an image inversion prevention tag;
   retrieving an acquired medical image associated with the patient anatomy from a data store based in part on the patient marker, the acquired medical image comprising imaging acquired of one or more anatomical structures of the patient anatomy; and
   anchoring the acquired medical image to the patient anatomy based in part on the patient orientation marker;
   retrieving an augmentation tag from data storage, the augmentation tag associated with the patient marker and a location in the acquired medical image, the augmentation tag identifying at least one anatomical structure of the acquired medical image found at the location; and
   projecting, during the medical procedure, the acquired medical image and the augmentation tag onto lenses in an augmented reality headset to form a single graphical view which is overlaid on the patient anatomy viewable by the medical professional through the lenses of the augmented reality headset.

9. The non-transitory machine readable storage medium as in claim 8, further comprising matching the patient orientation marker with an image orientation marker in the acquired medical image to enable matching orientation of the acquired medical image with the patient orientation marker on the patient anatomy.

10. The non-transitory machine readable storage medium as in claim 8, further comprising using a visually scannable symbol attached to a patient to retrieve an identity of a patient and to enable retrieval of the acquired medical image associated with the visually scannable symbol.

11. The non-transitory machine readable storage medium as in claim 8, further comprising using the image inversion prevention tag to ensure the acquired medical image is not inverted with respect to the patient anatomy.

12. The non-transitory machine readable storage medium as in claim 8, further comprising:
   combining an endoscopic video feed with the single graphical view which is overlaid on the patient anatomy viewable by the medical professional through the lenses of the augmented reality headset; and
   using the augmentation tag to identify a size and shape of 3D structures in the endoscopic video feed and to match where an endoscope is estimated to be located in the patient anatomy using the augmentation tag.

13. A system for augmenting a view of patient anatomy during a medical procedure for a medical professional, comprising:
an augmented reality headset through which to view the patient anatomy during the medical procedure;
an augmentation processor in communication configured to:
capture morphometric measurements of the patient anatomy through the augmented reality headset during the medical procedure;
identify a patient marker of the patient anatomy using the augmented reality headset, the patient marker comprising information identifying a patient in order to retrieve pre-measured morphometric measurements;
retrieving pre-measured morphometric measurements associated with the patient anatomy from data storage using the patient marker identified using the augmented reality headset;
determine whether the morphometric measurements of patient anatomy match the pre-measured morphometric measurements associated with the patient anatomy as retrieved using the patient marker;
retrieving an acquired medical image associated with the patient anatomy as defined by the patient marker and matched morphometric measurements from data storage, the acquired medical image comprising imaging acquired of one or more anatomical structures;
aligning the acquired medical image with the view provided by the augmented reality headset during the medical procedure of the patient anatomy using the morphometric measurements; and
form a single graphical view with the acquired medical image and an augmentation tag, the augmentation tag identifying at least one anatomical structure of the acquired medical image; and
project the single graphical view formed from the acquired medical image and the augmentation tag onto lenses overlaid on the view of the patient anatomy during the medical procedure.

14. The system as in claim 13, wherein the morphometric measurements are shape, width, height, depth and contour of an appendage or patient anatomy.

15. The system as in claim 13, wherein the acquired medical image is a MRI, CT scan, X-ray, ultrasound, or photographic images internal to a human body.

16. The system as in claim 13, wherein the acquired medical image is displayed using the augmented reality headset with the acquired medical image projected on a semi-transparent optical imaging area.

17. The system as in claim 13, further comprising matching a patient orientation marker with an image orientation tag in the acquired medical image to enable correct orientation of the acquired medical image with the patient anatomy.

18. The system as in claim 13, wherein the patient marker is a scannable symbol including at least one of: a 1D (one dimensional) bar code, a 2D (two dimensional) bar code, a picture, a custom generated geometric shape, or a RFID (radio frequency ID) used to retrieve an identity of the patient and to retrieve the acquired medical image.

19. The system as in claim 13, wherein the augmentation processor performs:
identifying an image inversion prevention tag; and
aligning the acquired medical image and patient anatomy using an image inversion prevention tag to ensure the acquired medical image is not inverted with respect to the patient anatomy.

* * * * *